United States Patent [19]

Wojtowicz et al.

[11] 4,145,543
[45] Mar. 20, 1979

[54] ALKALI METAL DICHLOROISOCYANURATE COMPOSITIONS

[75] Inventors: John A. Wojtowicz, Cheshire; William C. Herms, Meriden, both of Conn.

[73] Assignee: Olin Corporation, New Haven, Conn.

[21] Appl. No.: 721,261

[22] Filed: Sep. 8, 1976

[51] Int. Cl.² .......................................... C07D 251/36
[52] U.S. Cl. .................................................. 544/190
[58] Field of Search ..................... 260/248 C; 544/190

[56] References Cited
U.S. PATENT DOCUMENTS

| | | | |
|---|---|---|---|
| 3,364,146 | 1/1968 | Casey et al. | 544/190 |
| 3,501,468 | 3/1970 | Moore et al. | 260/248 |
| 3,803,144 | 4/1974 | Berkowitz | 260/248 C |
| 3,878,208 | 4/1975 | Carlson et al. | 260/248 |
| 3,894,017 | 7/1975 | Wojtowicz | 260/248 |
| 3,923,802 | 12/1975 | Mill | 260/248 |

Primary Examiner—John M. Ford
Attorney, Agent, or Firm—James B. Haglind; Donald F. Clements

[57] ABSTRACT

Alkali metal dichloroisocyanurate compositions having improved resistance to thermal decomposition comprise an alkali metal dichloroisocyanurate and a proportion of an alkali metal chloride where the proportion is from about 6 to about 14 percent by weight of the alkali metal dichloroisocyanurate. Water may be used to replace part of the alkali metal chloride proportion.

The compositions are suitable for use in bleaching and sanitizing applications.

7 Claims, No Drawings

ALKALI METAL DICHLOROISOCYANURATE COMPOSITIONS

This invention relates to alkali metal dichloroisocyanurate compositions. More particularly, this invention relates to alkali metal dichloroisocyanurate compositions having a lower susceptibility to a self-sustaining thermal decomposition reaction. Alkali metal dichloroisocyanurates are well-known products used in laundry, bleaching and sanitizing applications.

It is known to prevent decomposition of salts of dichloroisocyanuric acid upon exposure to intense heat by including an inert filler in an amount of at least 30 percent by weight as mentioned in U.S. Pat. No. 3,145,206, issued Apr. 18, 1964 to R. J. Fuchs et al. U.S. Pat. No. 3,145,206 further describes the addition of cyanuric acid or dichloroisocyanuric acid in amounts below about 25 percent by weight. The inclusion of large amounts of inert fillers is highly undesirable as the available chlorine content of the product is drastically reduced. Addition of cyanuric acid or dichloroisocyanuric acid results in reduced solubility for the alkali metal dichloroisocyanurate, making the product less desirable as a bleaching or sanitizing agent. Further, the incorporation of the above described agents requires additional blending and mixing operations which increase the cost of the resulting product.

One object of the present invention is to provide alkali metal dichloroisocyanurate compositions having a lower susceptibility to a self-sustaining thermal decomposition reaction.

Another object of the present invention is to provide alkali metal dichloroisocyanurate compositions having improved resistance to thermal decomposition which are readily soluble in aqueous solutions.

These and other objects of the invention will be apparent from the following description of the invention.

Briefly, the foregoing objects are accomplished in an alkali metal dichloroisocyanurate composition comprising an alkali metal dichloroisocyanurate and a proportion of an alkali metal chloride wherein the proportion of the alkali metal chloride is from about 6 to about 14 percent by weight of the alkali metal dichloroisocyanurate.

More in detail, suitable alkali metal dichloroisocyanurates which may be used in the composition of the present invention include sodium dichloroisocyanurate, potassium dichloroisocyanurate or lithium dichloroisocyanurate. The alkali metal dichloroisocyanurate may be in the form of the anhydrous salt or the monohydrate.

Alkali metal chlorides which may be employed in the compositions of the present invention include, for example, sodium chloride, potassium chloride and lithium chloride.

In the novel compositions of the present invention, the alkali metal chloride is present in amounts of from about 6 to about 14, and preferably from about 9 to about 12 percent by weight of the alkali metal dichloroisocyanurate.

These compositions are resistant to thermal decomposition, being non-propagating when contacted with, for example, a lighted match or cigarette.

The alkali metal present in the alkali metal chloride and the alkali metal dichloroisocyanurate may be the same, such as a composition comprising sodium dichloroisocyanurate and sodium chloride. However, the alkali metal of the alkali metal chloride may be different from the alkali metal of the alkali metal dichloroisocyanurate, for example, in compositions comprising sodium dichloroisocyanurate containing from about 6 to about 14 percent by weight of potassium chloride.

The novel compositions of the present invention may be produced in any desirable manner. U.S. Pat. No. 3,894,017, issued July 8, 1975, to J. A. Wojtowicz and W. Wolfe, Jr., describes the production of alkali metal dichloroisocyanurates such as sodium dichloroisocyanurate or lithium dichloroisocyanurate by reacting trichloroisocyanuric acid with sodium chloride or lithium chloride. Modification of this process to produce alkali metal dichloroisocyanurate compositions containing from about 6 to about 14 percent by weight of alkali metal chloride is quite feasible.

Similarly, the novel compositions of the present invention may be produced by reacting a monoalkali metal cyanurate with an alkali metal hypochlorite and chlorine in an aqueous medium to form a reaction mixture containing the alkali metal dichloroisocyanurate and an alkali metal chloride in the appropriate proportions. An additional method is the production of the alkali metal salt of dichloroisocyanuric acid by the reaction of an aqueous slurry of a monoalkali metal cyanurate with hypochlorous acid to produce a chloride-free slurry of the alkali metal dichloroisocyanurate. The slurry is filtered and the desired proportion of alkali metal chloride admixed with the filter cake. Compositions comprising alkali metal salts of dichloroisocyanuric acid and controlled amounts of an alkali metal chloride may thus be obtained, by the admixture of the alkali metal chloride with the dichloroisocyanurate in any suitable manner. For example, the desired proportion of alkali metal chloride is blended with anhydrous alkali metal dichloroisocyanurate. In another embodiment, the alkali metal dichloroisocyanurate is coated with the alkali metal chloride, for example, by spray graining.

The novel compositions of the present invention have a high available chlorine content. For example, the compositions contain from about 85 to about 94 percent of the available chlorine content of that of the alkali metal dichloroisocyanurate. When anhydrous sodium dichloroisocyanurate (theoretical available chlorine content 64.5%) is the alkali metal dichloroisocyanurate, compositions of the present invention containing from about 6 to about 14 percent by weight sodium chloride have an available chlorine content from about 54% to about 60.5%. The compositions of the present invention are readily soluble in aqueous solutions and are resistant to thermal decomposition when subjected to an intense source of heat, e.g., a lighted match or cigarette.

In an added embodiment, a portion of the alkali metal chloride in the novel compositions of the present invention may be replaced by water provided that the combined weight of the alkali metal chloride and the water do not exceed 14 percent by weight of the alkali metal dichloroisocyanurate. For example, suitable compositions include those containing from about 6 to about 10 percent of alkali metal chloride and from about 8 to about 4 percent water based on the weight of the alkali metal dichloroisocyanurate.

The novel compositions of the present invention, which are suitably used in bleaching and sanitizing applications, are further illustrated by the following examples. All percentages used are by weight unless otherwise specified.

EXAMPLES 1–5

Five mixtures of anhydrous sodium dichloroisocyanurate and sodium chloride were prepared in which the proportion of sodium chloride was 6, 8, 10, 12 and 14 percent by weight of the sodium dichloroisocyanurate, respectively. Four portions of each mixture were tested for flame propagation by contacting each portion with a lit match. The results are reported in Table 1 below.

Comparative Test 1

A mixture of anhydrous sodium dichloroisocyanurate and sodium chloride was prepared in which the proportion of sodium chloride was 4 percent by weight of the sodium dichloroisocyanurate. Four portions of this mixture were tested for flame propagation by contacting each portion with a lit match. Flame propagation occurred in each portion, as reported in Table 1 below for Example Cl.

hypochlorite. The controlled addition of the reactants maintained the pH of the reaction mixture at 6.5 ± 0.2. A reaction temperature of about 15° C. was maintained by circulating cooling water through a jacket surrounding the chlorinator. During the reaction period, the reaction mixture was agitated. The reaction mixture was filtered and the filter cake was air dried and then oven dried to give an anhydrous sodium dichloroisocyanurate product containing 9.4 percent sodium chloride and having an available chlorine content of 56.2 percent. The product was non-propagating when contacted with a lit match.

What is claimed is:

1. A composition comprising sodium dichloroisocyanurate and a proportion of an alkali metal chloride wherein said proportion of said alkali metal chloride is from about 6 percent to about 14 percent by weight of said sodium dichloroisocyanurate.

2. The composition of claim 1 in which said alkali

TABLE I
FLAME PROPAGATION OF SODIUM DICHLOROISOCYANURATE - SODIUM CHLORIDE MIXTURES

| Example No. | Anhydrous Sodium Dichloroisocyanurate (a) (% by weight) | Sodium Chloride (% by weight) | % AV. Cl CALC'D. | % AV. Cl FOUND | Flame Propagation I Contact With Lit Match (Four Tests) |
|---|---|---|---|---|---|
| 1 | 94 | 6 | 60.6 | 60.5 | Non-propagation occurred in 3 of 4 tests |
| 2 | 92 | 8 | 59.3 | 58.5 | Non-propagation occurred in 3 of 4 tests |
| 3 | 90 | 10 | 58.1 | 57.5 | Non-propagation occurred in all 4 tests |
| 4 | 88 | 12 | 56.8 | 55.6 | Non-propagation occurred in all 4 tests |
| 5 | 86 | 14 | 55.5 | 54.1 | Non-propagation occurred in all 4 tests |
| Cl | 96 | 4 | 61.9 | 61.0 | Propagation occurred in all 4 tests |

(a) Sodium dichloroisocyanurate contained less than 1% by weight of water

EXAMPLE 6

A homogeneous mixture was prepared comprising 86 percent by weight of anhydrous sodium dichloroisocyanurate, 6 percent by weight of sodium chloride, 8 percent by weight of water and having an available chlorine content of 55.5 percent. The mixture was exposed to the flame of a Bunsen burner. No propagation of burning occurred.

EXAMPLE 7

The procedure of Example 6 was repeated using a homogeneous mixture comprising 86 percent by weight of anhydrous sodium dichloroisocyanurate, 10 percent by weight of sodium chloride, 4 percent by weight of water and having an available chlorine content of 54.3 percent. When exposed to the flame of a Bunsen burner, the mixture was non-propagating.

EXAMPLE 8

An aqueous 50 percent monosodium cyanurate monohydrate slurry was pumped to a chlorinator. Simultaneously added to the chlorinator was gaseous chlorine and a 13 percent aqueous solution of sodium metal chloride is sodium chloride.

3. The composition of claim 2 in which said proportion of said sodium chloride is from about 9 to about 12 percent by weight of said sodium dichloroisocyanurate.

4. The composition of claim 3 in which said sodium dichloroisocyanurate is anhydrous sodium dichloroisocyanurate.

5. A composition comprising an alkali metal dichloroisocyanurate, a proportion of an alkali metal chloride wherein said proportion of said alkali metal chloride is from about 6 to about 14 percent by weight of said alkali metal dichloroisocyanurate, and containing water in an amount such that the combined weight of said alkali metal chloride and said water does not exceed 14 percent by weight of said alkali metal dichloroisocyanurate.

6. The composition of claim 5 in which said alkali metal dichloroisocyanurate is sodium dichloroisocyanurate and said alkali metal chloride is sodium chloride.

7. The composition of claim 6 in which said water is from about 4 to about 8 percent by weight of said sodium dichloroisocyanurate.

* * * * *